(12) United States Patent
McAuley et al.

(10) Patent No.: US 10,004,865 B2
(45) Date of Patent: *Jun. 26, 2018

(54) MASK

(71) Applicant: Fisher & Paykel Healthcare Limited, Auckland (NZ)

(72) Inventors: Alastair Edwin McAuley, Dallas, TX (US); Christopher Earl Nightingale, Auckland (NZ); Aidan Mark Shotbolt, Dunedin (NZ); Ivan Milivojevic, London (GB)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/156,073

(22) Filed: May 16, 2016

(65) Prior Publication Data

US 2016/0310687 A1 Oct. 27, 2016

Related U.S. Application Data

(63) Continuation of application No. 14/832,271, filed on Aug. 21, 2015, now Pat. No. 9,339,621, which is a (Continued)

(30) Foreign Application Priority Data

Sep. 3, 2003 (NZ) ........................................ 528029

(51) Int. Cl.
 *A61M 16/06* (2006.01)
 *A61M 16/20* (2006.01)
 *A61M 16/00* (2006.01)

(52) U.S. Cl.
 CPC ............ *A61M 16/06* (2013.01); *A61M 16/00* (2013.01); *A61M 16/024* (2017.08); (Continued)

(58) Field of Classification Search
 CPC ...... A61M 16/00; A61M 16/06; A61M 16/20; A61M 16/208; A61M 16/209; A61M 2016/0661; A61M 39/22; A61M 2039/2426; A61M 2205/42; A62B 9/00; A62B 9/02; A62B 9/04; A62B 18/00; A62B 18/10
 (Continued)

(56) References Cited

U.S. PATENT DOCUMENTS 3,890,966 A 6/1975 Aspelin et al.
3,982,532 A 9/1976 Halldin et al.
(Continued)

FOREIGN PATENT DOCUMENTS

EP 1 245 250 A2 10/2002
JP 2000-325481 A 11/2000
(Continued)

*Primary Examiner* — Colin W Stuart
(74) *Attorney, Agent, or Firm* — Knobbe Martens Olson & Bear LLP

(57) ABSTRACT

A mask is disclosed that has a gas outlet which is quiet and provides for a diffused outlet flow of gases. The outlet is preferably a slot formed between a hollow body and cover over said hollow body. The mask also preferably extends and seals under a user's chin in use.

17 Claims, 10 Drawing Sheets

Related U.S. Application Data continuation of application No. 14/270,200, filed on May 5, 2014, now Pat. No. 9,144,655, which is a continuation of application No. 10/570,226, filed as application No. PCT/NZ2004/000194 on Aug. 20, 2004, now Pat. No. 8,714,157.

(52) U.S. Cl.
CPC ...... *A61M 16/0622* (2014.02); *A61M 16/208* (2013.01); *A61M 2205/42* (2013.01)

(58) Field of Classification Search
USPC .................. 128/205.25, 206.21, 207.12
See application file for complete search history.

(56) References Cited

U.S. PATENT DOCUMENTS

| | | |
|---|---|---|
| 4,706,683 A | 11/1987 | Chilton et al. |
| 4,974,586 A | 12/1990 | Wandel et al. |
| 5,243,971 A | 9/1993 | Sullivan et al. |
| 5,758,642 A | 6/1998 | Choi |
| 6,112,746 A | 9/2000 | Kwok et al. |
| 6,435,181 B1 | 8/2002 | Jones, Jr. et al. |
| 6,460,539 B1 | 10/2002 | Japuntich et al. |
| 6,561,191 B1 | 5/2003 | Kwok |
| 6,581,594 B1 | 6/2003 | Drew et al. |
| 6,584,977 B1 | 7/2003 | Serowski |
| 6,736,139 B1 | 5/2004 | Wix |
| 6,851,425 B2 | 2/2005 | Jaffre et al. |
| 7,066,178 B2 | 6/2006 | Gunaratnam et al. |
| 7,089,939 B2 | 8/2006 | Walker et al. |
| 8,714,157 B2 | 5/2014 | McAuley et al. |
| 9,144,655 B2 | 9/2015 | McAuley et al. |
| 9,339,621 B2 | 5/2016 | McAuley et al. |
| 2002/0014241 A1 | 2/2002 | Gradon et al. |
| 2003/0037788 A1* | 2/2003 | Gallem ............. A61M 16/08 128/206.21 |

FOREIGN PATENT DOCUMENTS

| | | |
|---|---|---|
| RU | 2186597 C1 | 8/2002 |
| SU | 726692 A1 | 9/1981 |
| WO | WO 00/78381 | 12/2000 |

\* cited by examiner

MASK

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

The present application is a continuation application of U.S. application Ser. No. 14/832,271, filed Aug. 21, 2015, which is a continuation application of U.S. application Ser. No. 14/270,200, filed May 5, 2014 now U.S. Pat. No. 9,144,655, which is a continuation application of U.S. application Ser. No. 10/570,226, filed Nov. 1, 2006 now U.S. Pat. No. 8,714,157, which is a national phase filing of PCT Application No. PCT/NZ2004/000194, filed Aug. 20, 2004, which claims a priority benefit to New Zealand Patent Application No. 528029, filed Sep. 3, 2003, each of which is incorporated herein by reference in its entirety.

BACKGROUND OF THE INVENTION

Field of the Invention

This invention relates to the delivery of respiratory gases, and in particular to patient interfaces for providing gases to patients requiring respiratory therapy.

Summary of the Prior Art

In the art of respiration devices, there are well known a variety of respiratory masks which cover the nose and/or mouth of a human user in order to provide a continuous seal around the nasal and/or oral areas of the face such that gas may be provided at positive pressure within the mask for consumption by the user. The uses for such masks range from high altitude breathing (i.e., aviation applications) to mining and fire fighting applications, to various medical diagnostic and therapeutic applications.

One requisite of such respiratory devices has been that they provide an effective seal against the user's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

Where such masks as those used above are used in respiratory therapy, in particular treatment of obstructive sleep apnea (OSA) using Continuous Positive Airway Pressure (CPAP) therapy, there is generally provided in the art a vent for washout of the bias flow or expired gases to the atmosphere. Such a vent may be provided for example, as part of the mask, or in the case of some respirators where a further conduit carries the expiratory gases, at the respirator. The washout of gas from the mask is essential to ensure that carbon dioxide build up does not occur over the range of flow rates. In the typical flow rates in CPAP treatment, usually between 4 cm $H_2O$ to 20 cm $H_2O$, prior art attempts at such vents have resulted in excessive noise causing irritation to the user and concentrated flows of gases irritating any bed partners.

Various approaches have been developed in the prior art to attempt to reduce the noise by using slots to disperse the escaping gases when CPAP therapy is provided. For example, U.S. Pat. No. 6,460,539 and U.S. Pat. No. 3,890,966. However, these prior art methods are not entirely satisfactory in eliminating the extra noise created by a vent at the mask.

SUMMARY OF THE INVENTION

It is an object of the present invention to attempt to provide a mask which goes some way to overcoming the abovementioned disadvantages in the prior art or which will at least provide the industry with a useful choice.

Accordingly in a first aspect the invention consists in a device for delivering a supply of gases to a user comprising:

a mask, in use in fluid communication with said supply of gases and supplying said gases to said user, at least one outlet member integrated with or attached to said mask, wherein the boundary between said outlet member and said mask forms at least one narrow outlet vent that in use passes a substantial portion of the expired gases of said user, said outlet vent comprises a slot formed in said mask and a cover extending over said slot and attached to said mask, such that the separation between said mask and said cover increases to the edge of said cover in order to diffuse said exhaled gases.

Preferably said outlet member is removable.

Preferably said at least one outlet vent is a substantially long tapered slot.

Alternately said at least one outlet vent is a substantially circular hole.

Preferably said at least one outlet vent extends between the top and bottom of said mask.

Preferably said mask is a nasal mask.

Preferably said mask is a full face mask.

In a further aspect the present invention consists in a CPAP system for delivering gases to a user including a pressurised source of gases, transport means in fluid communication with said pressurised source adapted to convey said gases, and a mask in fluid communication with said transport means in use delivering said gases to said user, said mask including:

at least one outlet member integrated with or attached to said mask, wherein the boundary between said outlet member and said mask forms at least one long narrow tapered slot that in use passes a substantial portion of the expired gases of said user, wherein said outlet vent comprises a slot formed in said mask and a cover extending over the slot and attached to the mask, such that the separation between the mask and the cover increases to the edge of the cover in order to diffuse said exhaled gases.

Preferably said outlet member is removable.

In a further aspect the present invention consists in an outlet member for a gases delivery mask, said mask including at least one said outlet member, the boundary between said outlet member and said mask forms at least one narrow outlet vent that in use passes a substantial portion of expired gases from a user, wherein the outlet member comprises a cover extending over a slot in the mask and attached to the mask, such that the separation between the mask and the cover increases to the edge of the cover in order to diffuse the exhaled gases.

BRIEF DESCRIPTION OF THE DRAWINGS

The preferred form of the present invention will now be described with reference to the accompanying drawings.

DETAILED DESCRIPTION OF THE PREFERRED EMBODIMENT

The present invention provides improvements in the field of CPAP therapy. In particular to a mask with a gas outlet is described which is quieter and has a more diffused outlet flow. In addition the manufacture of the gas outlet on a mask is simpler; it does not suffer to the same extent from excessive manufacturing faults. It will be appreciated that the mask as described in the preferred embodiment of the present invention can be used in respiratory care generally or with a ventilator but will now be described below with reference to use in a humidified CPAP system. It will also be appreciated that the outlet vent described is equally applicable to all forms of patent interface. It will also be appreciated that the outlet vent described can be used with various forms of mask, it is not limited to use with full face masks, but is described below with reference to full face masks.

The full face mask of the present invention also has the added benefit of extending under the chin of the patient in use, and as such patients do not require a chin strap, as is the case with some prior art masks.

Figure 1:
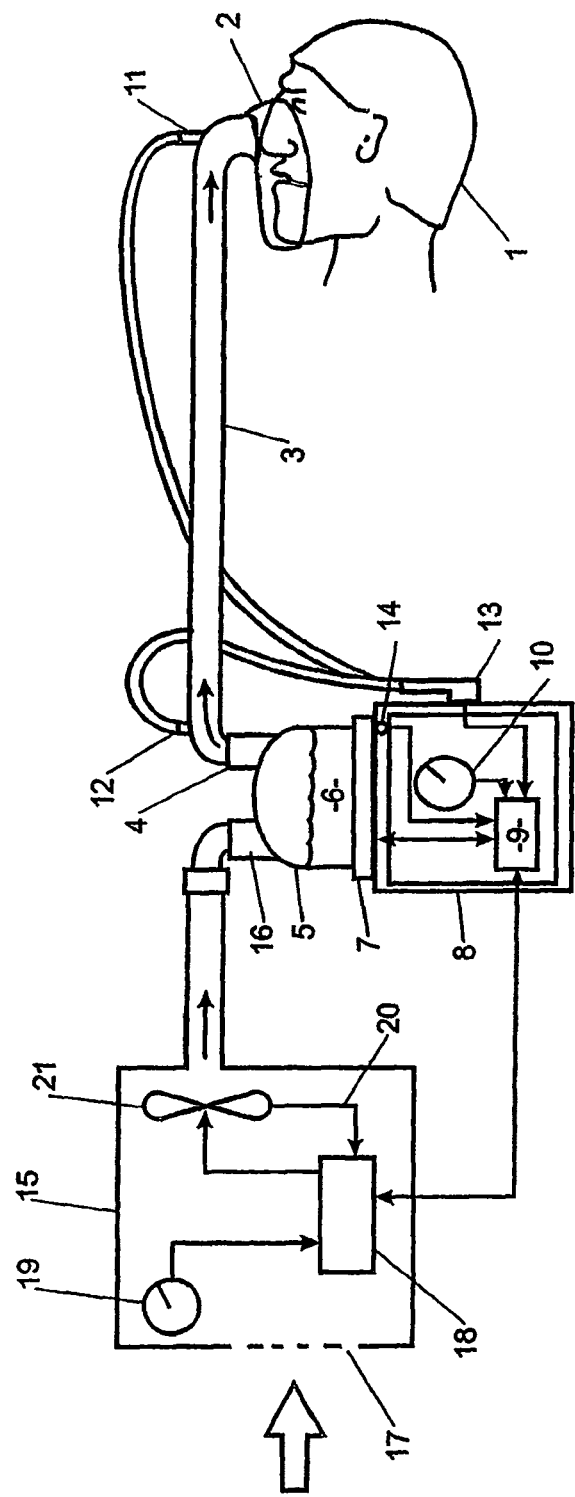
FIG. 1 is a block diagram of a humidified continuous positive airway pressure (CPAP system) as might be used in conjunction with the mask of the present invention.
Figure 2:
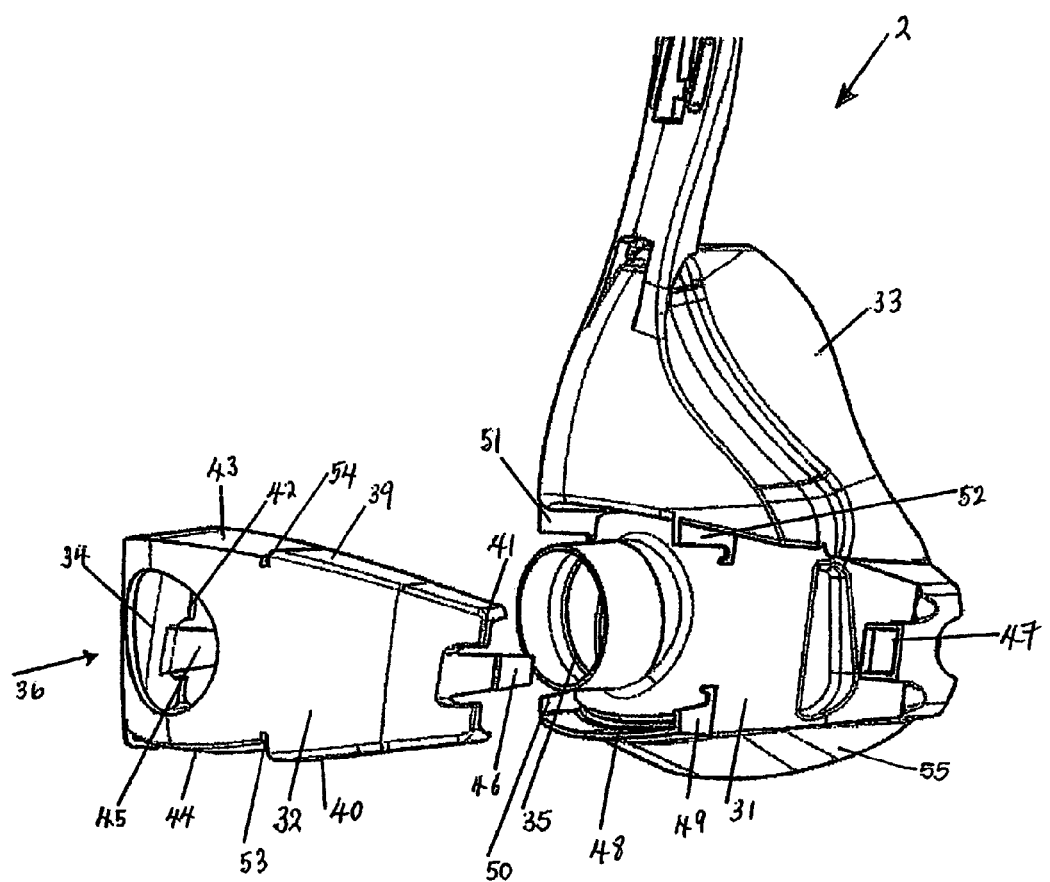
FIG. 2 is a perspective exploded view of the mask and outlet member of the preferred embodiment of the mask of the present invention.

With reference to FIG. 1 a humidified Continuous Positive Airway Pressure (CPAP) system is shown in which a patient 1 is receiving humidified and pressurised gases through a patient interface, for example a full face mask 2 (as shown in FIG. 2) or other appropriate types of patient interfaces, such as nasal masks. The patient interface 2 is connected to a humidified gases transportation pathway or inspiratory conduit 3. It should be understood that delivery systems could also be VPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5 which contains a volume of water 6. Inspiratory conduit 3 may contain heating means or heater wires (not shown) which heat the walls of the conduit to reduce condensation of humidified gases within the conduit. Humidification chamber 6 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (preset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. Exhaled gases from the patient's mouth exit through vents in the mask and are passed to ambient surroundings, as shown in FIG. 1.

Blower 15 is provided with variable pressure regulating means or variable speed fan 21 which draws air or other gases through blower inlet 17. The speed of variable speed fan 21 is controlled by electronic controller 18 (or alternatively the function of controller 18 could carried out by controller 9) in response to inputs from controller 9 and a user set predetermined required value (preset value) of pressure or fan speed via dial 19.

Figure 13:
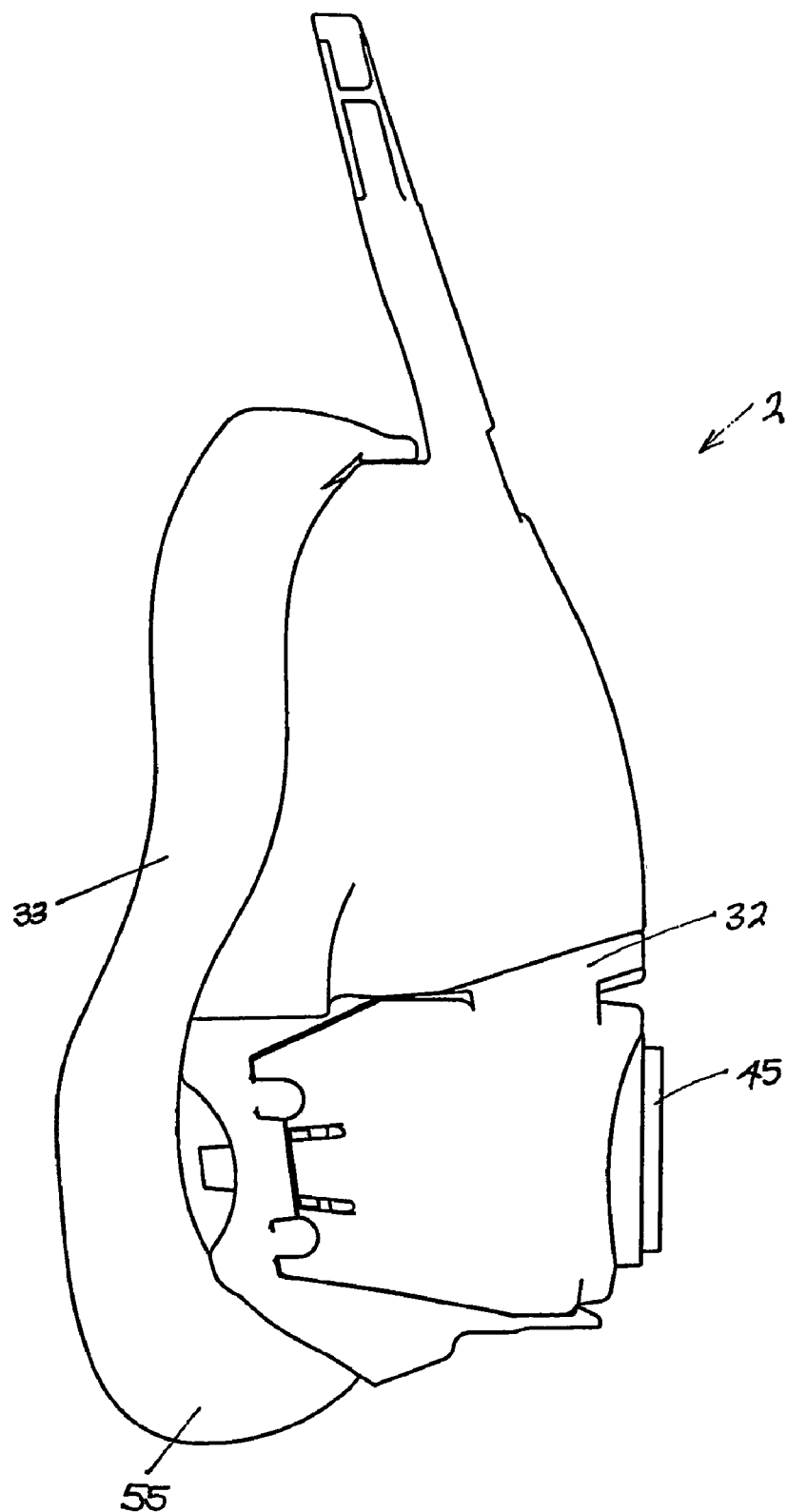
FIG. 13 is a side view of the mask of FIG. 2, where the mask is shown to have a cushion that rests in use against and users face.

Referring to FIGS. 2 and 13 a patient interface that is a full face mask is shown in detail. The mask 2 includes a hollow body 30 and mask cushion 33. The mask cushion 33 resides within the hollow body 30 and provides cushioning of the mask 2 or the patient's face. The hollow body and mask cushion are shown in FIGS. 1 and 13 as extending under the patients chin, in particular, in the area indicated as 55. The extension under the chin of the cushion 33 provides a good seal and renders unnecessary a chin strap.

The hollow body 30 has an integrally formed recess 31. The recess 31 preferably extends longitudinally along and over the width of the mask body 30 but may not extend the full width of the mask as shown in FIG. 2. Further the recess 31 may not be a longitudinal recess but lateral or other orientation. An outlet member or insert 32 is fittable about or in the recess. The insert 32 substantially covers the whole of the recess 31. The recess 31 and insert 32 each have complimentary circular apertures 34, 35 that form an inspiratory inlet 36 when the insert 32 is placed in the recess 30. The inlet 36 is capable of being connected to the tubing that forms the inspiratory conduit 3 (as shown on FIG. 1). Gases, supplied to the inspiratory conduit 3 from the CPAP device and humidifier, enter the mask through the apertures 34, 35 and the patient is able to breathe these gases. The mask 2 is positioned around the nose and mouth of the user 1 and headgear (not shown) may be secured around the back of the head of the patient 1 to assist in the maintaining of the mask on the patient's face. The restraining force from the headgear on the hollow body 30 ensures enough compressive force on the mask cushion 33 to provide an effective seal against the patient's face.

The hollow body 30 and insert 32 are injection moulded in a relatively inflexible material, for example, polycarbonate plastic. Such a material would provide the requisite rigidity for the mask as well as being transparent and a relatively good insulator.

Figure 3:
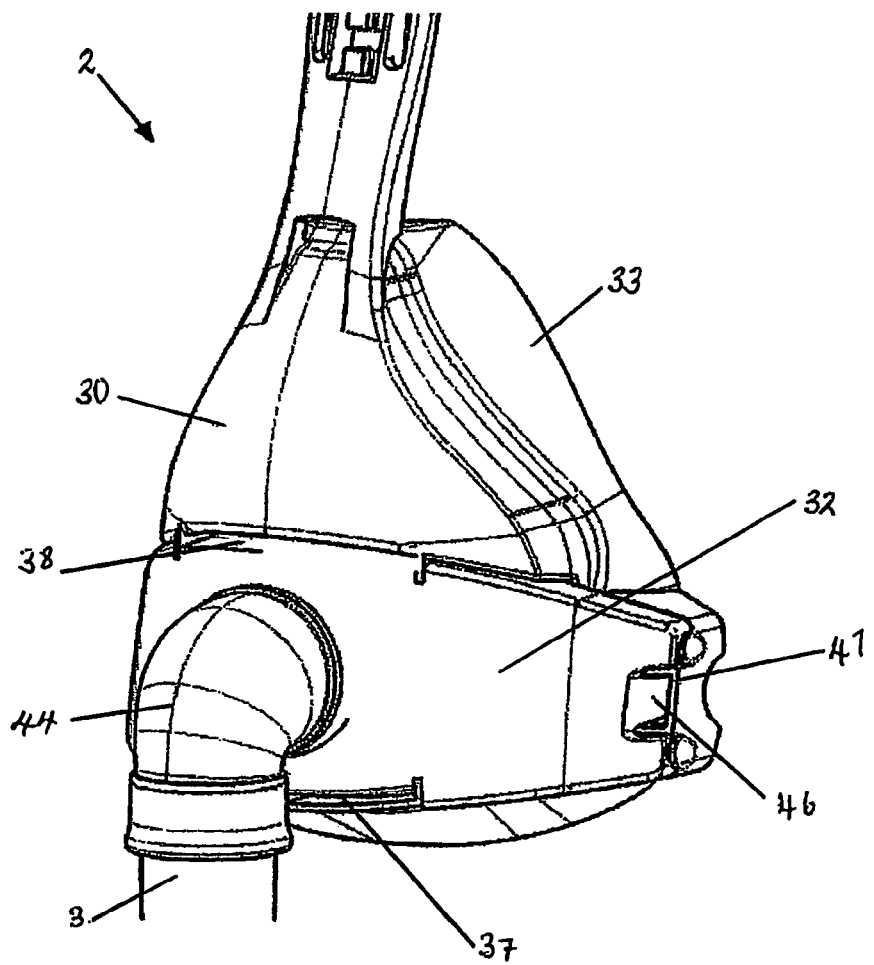
FIG. 3 is a perspective view of the mask of the present invention.

Referring to FIG. 3, when the insert 32 is in placed on the mask shell or hollow body 30 in the recess 31 narrow slots 37, 38 are created between the mask shell 30 and insert 32. These slots 37, 38 act as expiratory vents for gases expired in use into the mask by the patient wearing the mask.

In some forms of the mask of the present invention the insert 32 is removable, but in other forms the insert is welded in place to prevent removal.

The insert 32 and narrow slots or outlet vents 37, 38 will now be described in more detail. Referring to FIGS. 2 to 5, the insert 32 is curved to follow the contours of the mask shell 30 and has upper and lower sides 39, 40 that taper down towards the left and right sides 41, 42. Two elongated recesses 53, 54 are formed on the insert's upper and lower sides 39, 40. The recesses 53, 54 are shown as being formed in the middle section of the insert 32 near to the inspiratory aperture 34 and do not extend over the full length of the upper and lower sides 39, 40. In other forms the recesses (that form the expiratory vents) may extend along the full length of the upper and lower sides of the insert. Thus when the insert 32 attached or connected to the mask shell into the recess 31, formed at the boundary between the insert 32 and mask shell 30 are narrow outlet vents 37, 38.

To provide support to the insert 32, within the recess a number of walls are provided that the insert rests against. In particular, as shown in FIG. 2, a lower internal wall 48 having side walls 49, 50 extending upwards from it is formed at the lower edge of the recess 31. The lower outlet vent 37 is actually formed between the boundary of the lower wall 48 and the lower side of the insert 32. Upper internal sideways walls 52, 53 are also formed in the recess 31. These provide further support and each of the side walls 49, 50, 51, 52 fit within slots (of which only two slots 53, 54 of the four slots is shown in FIG. 2.

The insert 32 may be permanently fixed in the mask shell 30 by gluing, ultrasonic welding or other appropriate fastening methods. In other forms, and particularly that shown in FIG. 2, the insert 32 is removable from the mask shell 30 and is provided with clips 45, 46. The clips 45, 46 are fastenable in apertures (of which only one side aperture 47 is shown in FIG. 2) at the sides of the mask body 30. The clips merely need to be pushed inwards by a user to disengage them from the apertures 47 so that the insert 32 can be removed.

Figure 4:
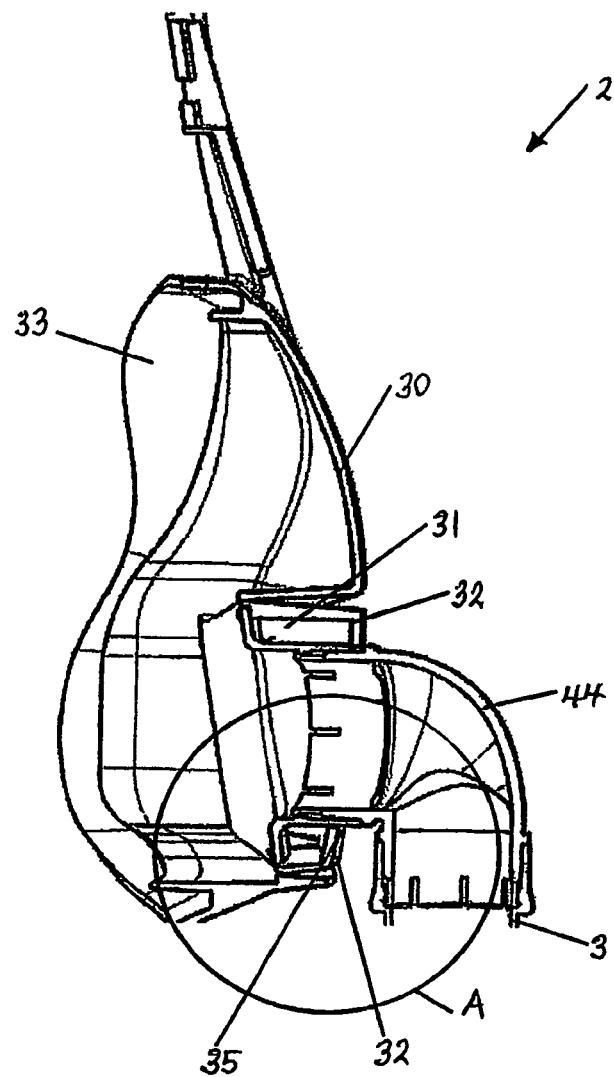
FIG. 4 is a side cross section of the mask and outlet member of the present invention.
Figure 5:
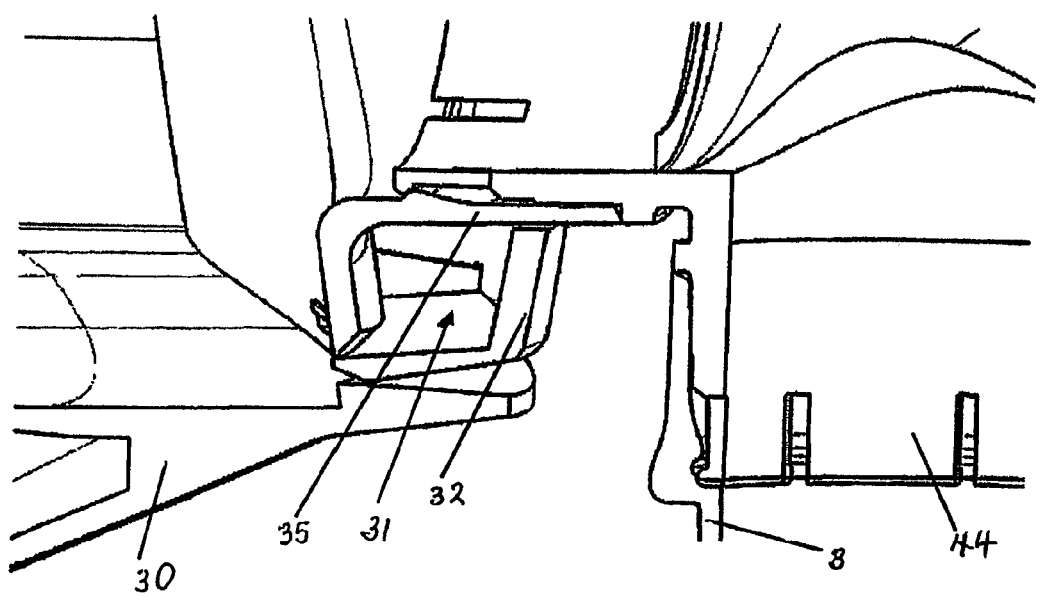
FIG. 5 is a close up view of detail A of FIG. 4 of the mask of the present invention.

FIGS. 3 to 5 show the mask of the present invention in an in use form where the insert 32 is attached to the mask shell 30 and a conduit 3 that is inserted and held within the inspiratory inlet 36 and aperture formed in the insert 32 and through the mask shell 30. The conduit 3 may be connected to an elbow connector 44, which may also be capable of swiveling within the aperture.

To ensure a proper seal around the outlet vents 37, 38 and between the insert 32 and mask shell 30 a plastics gasket, for example, one made of elastomer, such as silicon, may be provided between the insert 32 and mask shell 30. The gasket (not shown) would ensure sealing between these parts and reduce the noise of gases exiting the vents 37, 38.

It will be appreciated that by providing expiratory vents in the mask of the present invention effectively allows for minimising of the noise generated by the outward flow of expiratory gases form the mask, as well as reducing the noise level, the flow through the outlet vents is more diffused.

Figure 6:
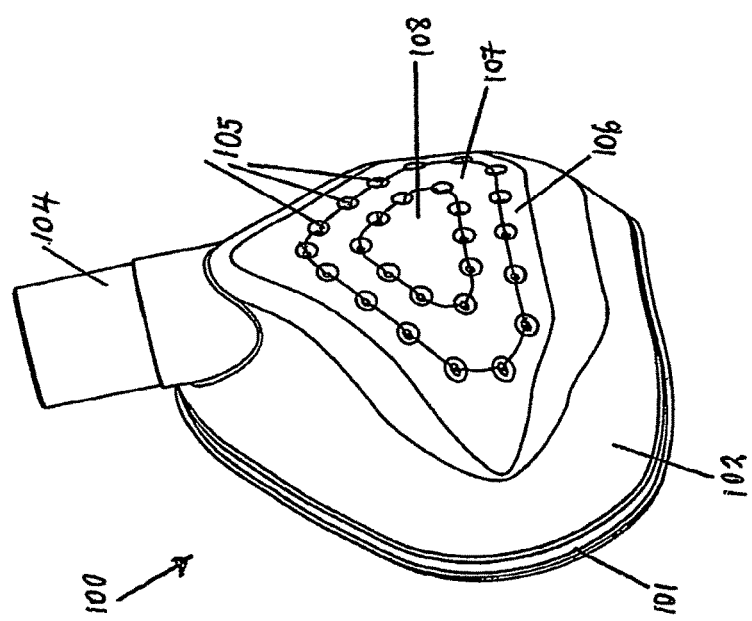
FIG. 6 is a perspective view of a first alternative form of the mask of the present invention.
Figure 7:
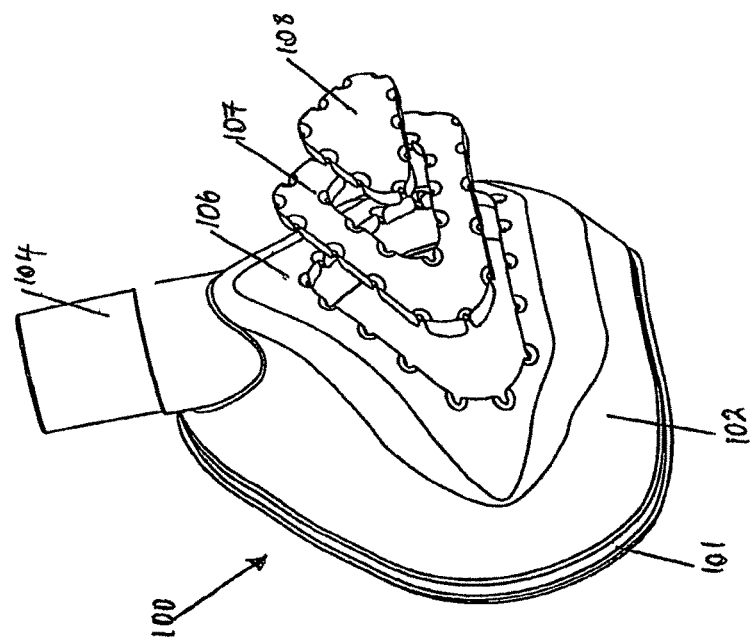
FIG. 7 is an exploded perspective view of the mask of FIG. 6.
Figure 8:
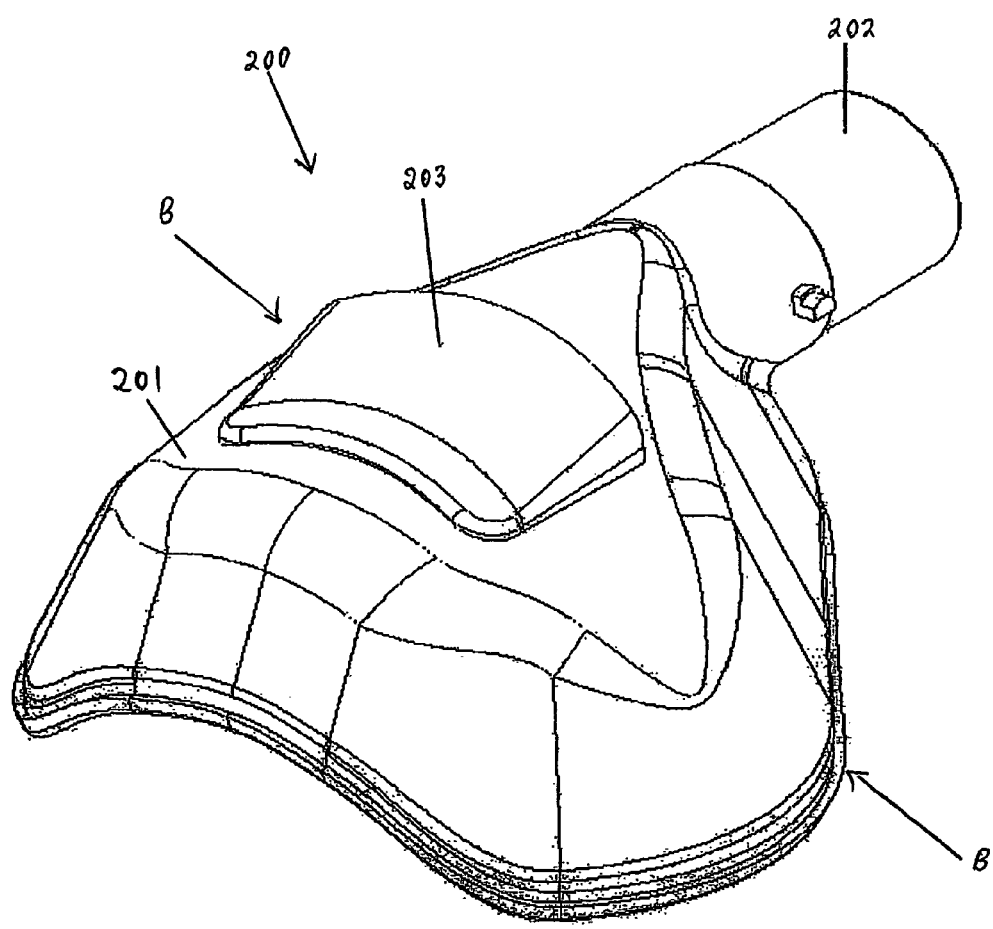
FIG. 8 is a perspective view of a second alternative form of the mask of the present invention.

An alternative form of the mask of the present invention is shown in FIGS. 6 and 7. The mask 100 has a cushion 101, body or shell 102 and a gases inlet 104 that receives gases from a conduit (for example conduit 3 as described with reference to FIG. 1). The mask shell 102 has a plurality of small diameter holes 105 in it that are ideally all directed away from the centre of the mask, i.e. diffusing or dispersing the flow of air. The holes 105 are shown in FIGS. 6 and 7 as being circular but in other forms of the mask they may be otherwise shaped. Furthermore, the holes may be straight through the mask or have an alternative section, for example they may be narrow nearer the inner side of the mask and broader in section nearer the outer side of the mask shell 103. In order to be able to mould small enough holes 105 in the mask shell 102, the mask shell is preferably split into two or more sections (for example, the three sections 106, 107, 108 as shown in FIG. 7) although more or less sections could be provided in some forms of the mask. The sections 106, 107, 108 are preferably joined together in any of the following ways, snap-lock, friction press fit, gluing, welding or any other appropriate fastening mechanism.

This form of the mask of the present invention would have the advantage that the plurality of holes 105 produces less noise but there is difficulty in moulding the sections 106, 107, 108.

A further alternative form of the mask of the present invention is illustrated in FIGS. 8 to 12. The mask 200 is similar to that described above and has a hollow body 201 and a cushion (not shown). The mask 200 is preferably a full face mask but may be a nasal mask or oronasal mask. The mask 200 has a gases inlet 202 that is capable of being connected to a conduit (such as inspiratory conduit 3, in FIG. 1) that supplies gases to the mask from a humidifier and blower as described earlier. In use when a patient is wearing the mask 201 they breathe in the gases entering the mask through the inlet 202 and exhale into the mask. To vent exhaled gases an outlet vent and/or diffuser 203 is provided on the outside of the mask hollow body 201. The outlet vent and/or diffuser 203 has an outlet member or cover 205 that extends over a slot or plurality of holes in the mask body 201.

This mask 200 has an alternative diffuser system where a narrow air gap 208 is formed between the outlet member 205 and the body 201, such that gases exhaled by the patient are forced through the air gap and diffused as they move out into the ambient air. In particular, a slot 204 (or series of holes, or any other means of allowing exhaled gases to exit the hollow body 201) are formed in the hollow body 201 and the outlet member 205, in the form of a cover is fitted about the slit 204. The cover 205 is substantially trapezoidal in shape and its bottom and side edges are fixed to the hollow body 201 of the mask 200. The bottom edge is substantially shorter in length than its top edges such that the width of the cover 203 increases from it's bottom to top edges. The cover 205 may be permanently fixed to the mask body (for example, by being welded, clipped or glued to the mask body 201) or may be able to be removed (for example, if the cover 205 was removably clipped to the mask body 201).

Figure 10:
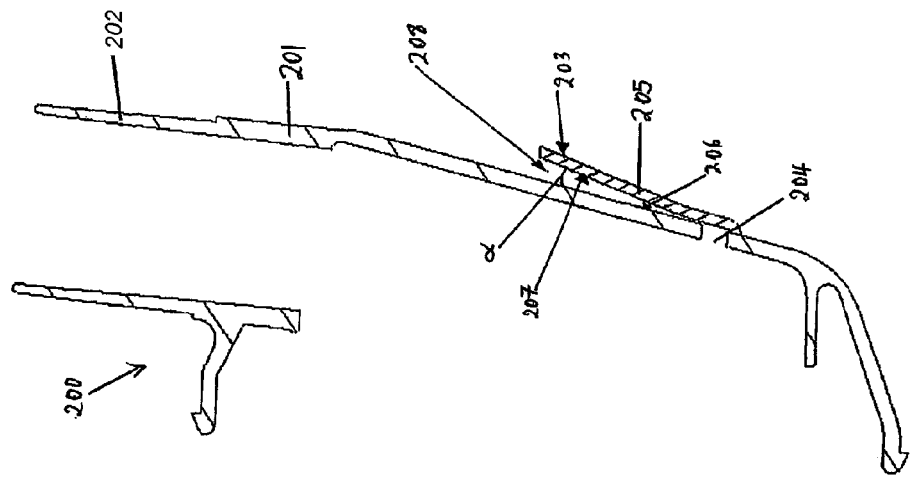
FIG. 10 is a cross-section through BB of the mask on FIG. 8.
Figure 9:
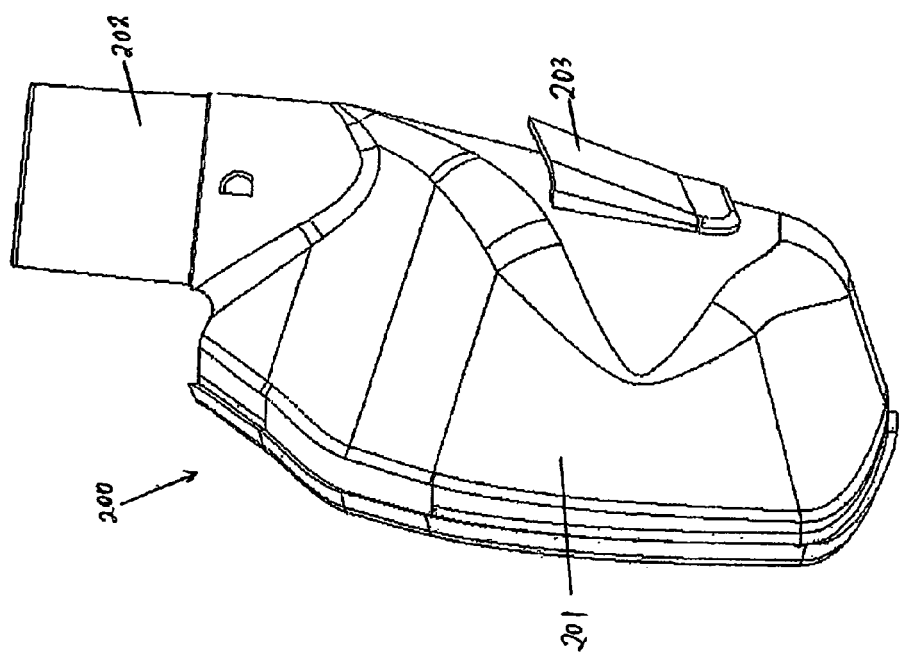
FIG. 9 is a side view of the mask of FIG. 8.

Referring to FIGS. 9 and 10, the front face of the cover 205 extends outwards from the mask body 201 such that an angle α (see FIG. 10) is formed between the mask body 201 and the front fact 205. This angle α is relatively low so that the gases exhaled by the patient that exit the gap 204 attach to the walls, in particular, the mask body wall 206 and the inner cover wall 207. With the gradual expansion in the area inside of the cover 205 the velocity of the gases passing through the air gap 208 reduces because the cross-sectional area of the gases flow increases as it moves out of the outlet member 203.

Figure 12:
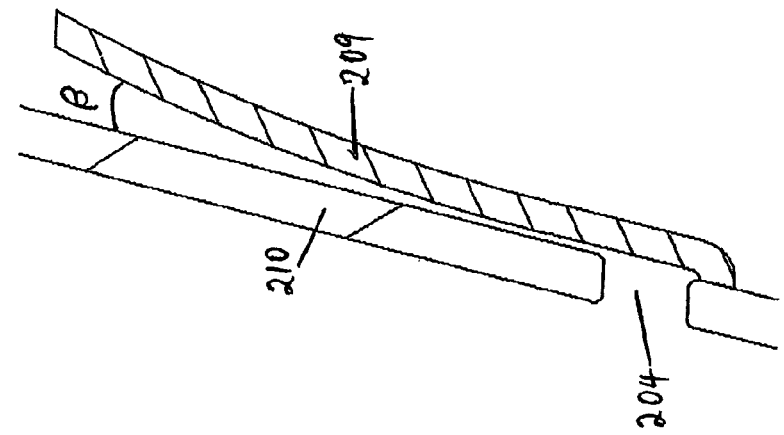
FIG. 12 is a close-up cross-section of a second form of the outlet member for use with the mask of FIG. 8, where the outlet member extends straight out from the mask body.
Figure 11:
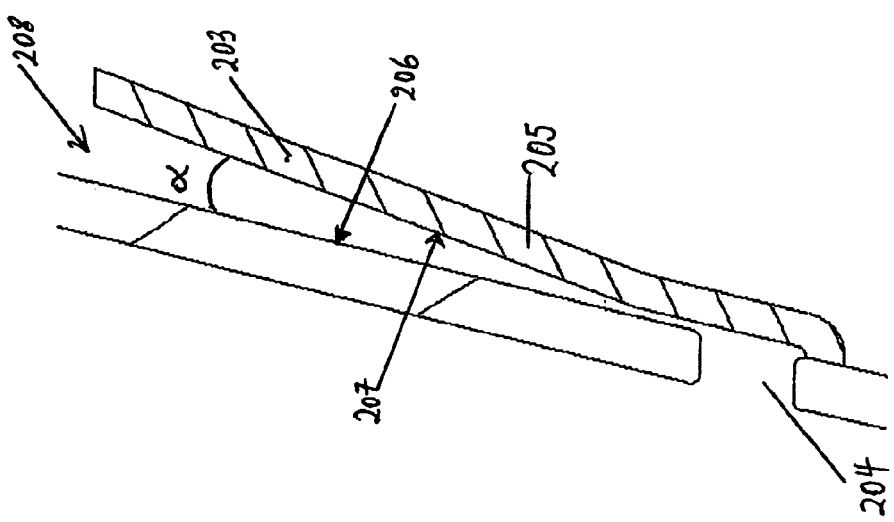
FIG. 11 is a close-up cross-section of a first form of the outlet member of the mask of FIG. 8, where the outlet member curves away from the mask body.

Referring now to FIGS. 11 and 12, in the preferred form of the mask of the present invention, the cover 205 may extend outwards from the mask body at a constant angle α, such as that shown in FIG. 11, so that the cover is substantially straight. In other forms of the cover (such as that cover 209 shown in FIG. 12) could be curved, so that the angle β between the mask body 210 and cover 209 gradually increases. It must be noted that the angle β will not exceed a predetermined angle, for example, it has been determined that angles greater than 20 degrees provide less than ideal diffusing of the exhales gases.

What is claimed is:

1. A mask for delivering a supply of gases to a user, the mask comprising:
    a mask cushion configured to contact a face of the user in use, the mask cushion being coupled to a hollow body;
    the hollow body having a front side and a back side, the back side facing toward the user in use and the front side facing away from the user in use, a gases inlet connected to the hollow body and being configured to deliver a flow of gases to the mask, the gases inlet being positioned along a central, vertically-extending bisecting plane that bisects the mask in half;
    the hollow body comprising:
        two sections configured to be joined together; and
        the two sections being configured such that, when the two sections are joined together, edges of the two sections cooperate to define a plurality of holes, at least a portion of the plurality of holes extending along an axis directed away from a center of the hollow body;
        the plurality of holes being configured to act as an expiratory vent for gases exhaled by the user into the mask.

2. The mask of claim 1, wherein the gases inlet is configured to be connected to a conduit, the conduit being configured to deliver gases to the gases inlet.

3. The mask of claim 1 further comprising a third section, the third section also being configured such that, upon alignment of the third section with either one or both of the two sections, a plurality of holes are defined along edges of the third section and the one or both of the two sections, and such that the third section combines with the two sections to define two or more sections.

4. The mask of claim 3, wherein the two or more sections are configured to be nested when joined together.

5. The mask of claim 1, wherein the two sections are configured to be fastened together.

6. The mask of claim 5, wherein the two sections are configured to be fastened together via a snap-lock.

7. The mask of claim 1, wherein each of the plurality of holes is formed at boundaries between the two sections when the two sections are joined together.

8. The mask of claim 7, wherein a first portion of each of the plurality of holes is formed at an edge of a first of the two sections and a second portion of each of the plurality of holes is formed at an edge of a second of the two sections configured to be adjacent the edge of the first of the two sections.

9. The mask of claim 1, wherein the mask is a full face mask.

10. The mask of claim 1, wherein the mask is a nasal mask.

11. A mask for delivering a supply of gases to a user, the mask comprising:
    a shell comprising two or more sections configured to be joined together, the shell comprising an inner surface and an outer surface;
    a plurality of holes formed at boundaries between the two or more sections when the two or more sections are joined together, each of the plurality of holes extending along an axis directed away from a center of the shell;
    a mask cushion coupled to the shell and configured to contact the face of the user in use;
    a gases inlet connected to the shell; and
    a conduit configured to connect to the gases inlet and deliver gases to the gases inlet;
    wherein a first portion of each of the plurality of holes is formed at an edge of a first of the two or more sections and a second portion of each of the plurality of holes is formed at an edge of a second of the two or more sections configured to be adjacent the edge of the first of the two or more sections.

12. The mask of claim 11, wherein the plurality of holes are configured to act as an expiratory vent for gases exhaled by the user into the mask.

13. The mask of claim 11, wherein the two or more sections are configured to be fastened together.

14. The mask of claim 13, wherein the two or more sections are configured to be fastened together via a snap-lock.

15. The mask of claim 11, wherein the two or more sections are configured to be nested when joined together.

16. The mask of claim 11, wherein the plurality of holes are circular.

17. The mask of claim 11, wherein the plurality of holes are straight and do not taper or expand along their length.

* * * * *